(12) United States Patent
Girardot et al.

(10) Patent No.: US 7,479,164 B2
(45) Date of Patent: Jan. 20, 2009

(54) CALCIFICATION-RESISTANT FIXATION

(75) Inventors: Jean-Marie Girardot, Dunwoody, GA (US); Marie-Nadia Girardot, Dunwoody, GA (US)

(73) Assignee: Biomedical Design, Inc., Marietta, GA (US)

( * ) Notice: Subject to any disclaimer, the term of this patent is extended or adjusted under 35 U.S.C. 154(b) by 566 days.

(21) Appl. No.: 10/892,924

(22) Filed: Jul. 16, 2004

(65) Prior Publication Data

US 2004/0253291 A1 Dec. 16, 2004

Related U.S. Application Data

(63) Continuation of application No. PCT/US03/01757, filed on Jan. 21, 2003.

(60) Provisional application No. 60/351,996, filed on Jan. 25, 2002.

(51) Int. Cl.
*A61L 27/00* (2006.01)
(52) U.S. Cl. .......................... 8/94.11; 8/94.33; 623/1.1; 623/2.1
(58) Field of Classification Search ............... 8/94.11, 8/94.33; 623/1, 2, 3, 11, 12, 13, 1.1, 2.1; 530/356, 326
See application file for complete search history.

(56) References Cited

U.S. PATENT DOCUMENTS

| 3,628,248 | A | | 12/1971 | Kroder et al. ............... 32/10 A |
|---|---|---|---|---|
| 4,378,224 | A | * | 3/1983 | Nimni et al. ................. 8/94.11 |
| 5,104,405 | A | * | 4/1992 | Nimni ......................... 600/36 |
| 5,374,539 | A | * | 12/1994 | Nimni et al. ............... 435/68.1 |
| 5,447,536 | A | | 9/1995 | Girardot et al. ............. 8/94.11 |
| 5,509,932 | A | | 4/1996 | Keogh et al. .................. 623/11 |
| 5,733,339 | A | | 3/1998 | Girardot et al. ............. 8/94.11 |
| 7,189,259 | B2 | * | 3/2007 | Simionescu et al. ........ 623/2.42 |

* cited by examiner

*Primary Examiner*—Lorna M Douyon
*Assistant Examiner*—Amina Khan
(74) *Attorney, Agent, or Firm*—Fitch, Even, Tabin & Flannery

(57) ABSTRACT

Non-glutaraldehyde fixation of an organ or a prosthesis for implantation in a mammal is based upon carbodiimide treatment. An aqueous solution containing a coupling agent, such as EDC, in combination with a coupling enhancer, such as sulfo-NHS, and a high concentration of a diamine cross-linking agent is used. As a result, only minimal surface reduction occurs during fixation, and the resultant products show a dramatic increase in resistance to calcification.

16 Claims, 4 Drawing Sheets

CALCIFICATION-RESISTANT FIXATION

This application is a continuation of International Application Ser. No. PCT/US03/01757, filed Jan. 21, 2003, which claims priority from U.S. Ser. No. 60/351,996, filed Jan. 25, 2002.

FIELD OF THE INVENTION

This invention relates to a process for fixing human or animal tissue prior to implantation, and more particularly to a fixation process which fixes tissue to render such tissue adequately resistant to enzymatic degradation with minimal shrinkage and in a manner so as to resist calcification.

BACKGROUND OF THE INVENTION

Calcification of glutaraldehyde-preserved or "fixed" bioprosthetic heart valves frequently occurs and leads to failure due to stenosis and regurgitation. In addition, the slow release of glutaraldehyde from the implanted device is cytotoxic. Several methods of tissue cross-linking or fixing that are independent of glutaraldehyde have been presented, and they include acyl azide, photooxidation, epoxy, genipin and carbodiimide. The latter is described in U.S. Pat. No. 5,733,339 issued Mar. 31, 1998. However, it is acknowledged that tissue shrinkage occurs during fixation, and no cross-linking method has yet been perfected that totally avoids tissue shrinkage (*J. Heart Valve Dis.* 2001; 10(1): 111-124). While this may be of no particular concern with respect to much pericardium or tissue for which tailoring will take place after fixation, it may well be an issue for porcine aortic root leaflets where precise interengagement, i.e. coaptation, is very important and excessive shrinkage may induce insufficient coaptation of the cusps which could render the valve incompetent. Therefore, the need for improved fixation technology that induces only minimum tissue shrinkage still exists, and the search for such technology has continued.

SUMMARY OF THE INVENTION

An improved fixation method based on water-soluble carbodiimide treatment has been found which results in tissue that is as effectively cross-linked as glutaraldehyde-fixed tissue, but that exhibits only minimal shrinkage as a result of fixation, and that exhibits surprisingly improved resistance to calcification after implantation in a mammal.

In a more particular aspect, the invention provides a process of fixing animal tissue to render it suitable for implantation in living mammals, which process comprises treating said animal tissue with an effective amount of a coupling agent which promotes the formation of amide bonds between reactive carboxyl moieties and reactive amino moieties, in combination with a coupling enhancer, and with a cross-linking agent containing at least two reactive amine moieties, said diamine cross-linking agent being present in an amount of at least about 80 millimolar, and said treatment being carried out in a manner which results in the formation of amidated links between said cross-linking agent and reactive moieties carried by the molecules of said animal tissue, whereby said tissue is rendered resistant to protease digestion while incurring only minimal surface reduction during fixation and whereby the fixed tissue is highly resistant to calcification.

In another particular aspect, the invention provides a process of fixing fresh animal tissue to render it suitable for implantation in living mammals, which process comprises washing but not otherwise altering fresh tissue excised from a donor animal, treating said washed animal tissue with an effective amount of a cross-linking agent containing at least two reactive amine moieties and with a coupling agent in combination with a coupling enhancer, which promotes the formation of amide bonds between reactive carboxyl moieties and reactive amino moieties, said diamine cross-linking agent being present in an amount of at least about 80 millimolar, and said treatment being carried out in a manner which results in the formation of amidated links between said cross-linking agent and reactive moieties carried by the molecules of said animal tissue, whereby said tissue is rendered resistant to protease digestion while incurring only minimal surface reduction during fixation and whereby the fixed tissue is highly resistant to calcification.

In a further particular aspect, the invention provides a prosthesis formed at least partially of animal tissue containing cross-links between and within the proteinaceous molecules of said tissue, which cross-links are comprised of amide bonds between reactive moieties on said tissue and additional amide bonds between reactive moieties on said tissue and diamine cross-linking agents having a carbon chain length of at least 4 carbon atoms, said cross-linking having been achieved by subjection of said tissue to an aqueous solution containing an effective amount of a water-soluble coupling agent which promotes the formation of amide bonds, a coupling enhancer and a concentration of between about 80 and about 130 millimolar of said diamine cross-linking agent.

DETAILED DESCRIPTION OF THE PREFERRED EMBODIMENTS

Figure 1:
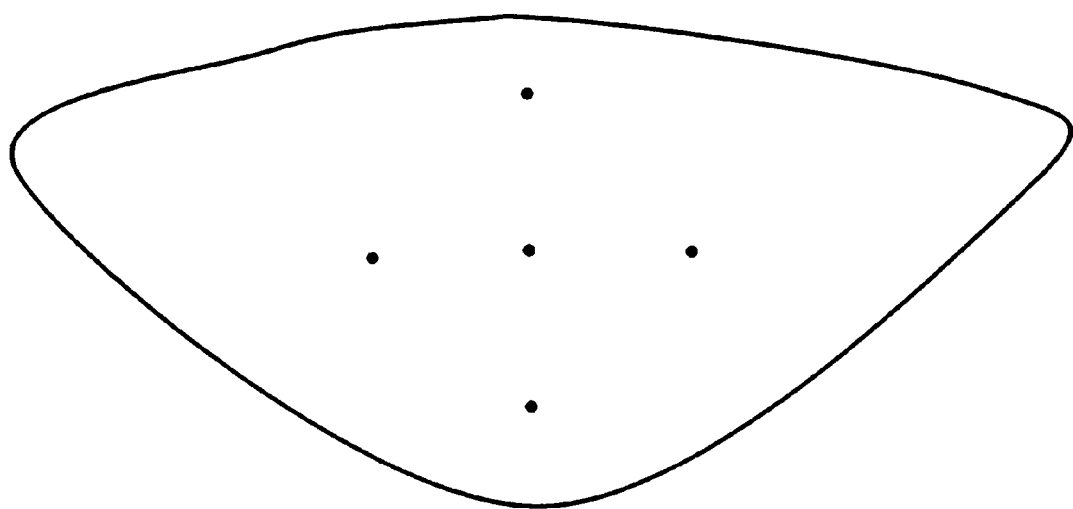
FIG. 1 is a view of a porcine aortic leaflet showing dots that indicate the marking that was carried out to measure the amount of surface reduction which occurs during fixing.

The basic fixation process with which the present invention is concerned is described in U.S. Pat. No. 5,733,339, the disclosure of which is incorporated herein by reference. It was surprisingly found that, by very substantially increasing the amount of diamine cross-linking agent, dramatic effects can be achieved using the basic carbodiimide cross-linking process.

As used herein, the term "bioprosthetic tissue" is meant to include any organ or tissue which is derived in whole or in part from a human or an animal, or which is produced from other organic tissue, and which is to be implanted, either by itself or as part of a bioprosthesis, in a human or in an animal. Thus, the term generally includes bioprosthetic tissue such as hearts, heart valves and other heart components, pericardium, vascular grafts, urinary tract and bladder components, tendons, bowel, and soft tissues in general, such as skin, collagen and the like. Although the prosthetic tissue will very often be one which is made from natural tissues, including but not limited to bovine, ovine, porcine and possibly even human tissue, other natural materials, well known to those having ordinary skill in this art, also can be used.

The one-step fixation method described herein consists of stabilizing the bioprosthetic tissue by binding reactive carboxyl moieties of the tissue either to a reactive amine moiety on the tissue or to a cross-linking agent, in such a manner as to leave few active moieties on or within the tissue.

The term "cross-linking", as used herein, refers to the fixation of bioprosthetic tissue that results from the formation of links of various lengths within and between the molecules of the tissue, such links resulting from amide bond formation either (a) between two reactive moieties of the tissue, thus forming short covalent links within and between the molecules of the tissue, or (b) between reactive moieties on the tissue and a covalently bound cross-linking agent.

The term "cross-linking agent" is used herein to describe a diamine having at least two free primary amine groups, preferably at each of its ends, which is capable of forming amide bonds with carboxyl groups on the proteinaceous animal tissue. It should preferably be a straight chain or a branched compound having from 4 to 12 carbon atoms; alternatively, but perhaps less desirably, carbocyclic compounds can be employed where the reactive amine moieties appropriately located on the ring, such as 2,4,6-triaminobenzene. More preferably, a di- or triamino cross-linking agent is chosen which has a molecular weight of about 190 or less and preferably about 150 or less so as to assure adequate penetration into the fresh tissue usually being treated. Most preferably, it is a straight chain from 6 to 8 carbon atoms in length with one reactive amine located at each end. Although the cross-linking agent may have optional substitutions along its length, it is preferably hydrocarbon that is substituted only with the reactive amines, e.g. a straight chain alkane having amines at each extremity. Preferred agents are 1,6-hexanediamine and 1,7-heptanediamine.

The terms "coupling agent" and "coupling enhancer", as used herein, refer to reagents that respectively promote and enhance the formation of amide bonds. These bonds may be formed between a reactive amine and a reactive carboxyl on the tissue (thus linking two such closely located reactive groups), or between a reactive amine on a cross-linking agent and a reactive carboxyl on or within the tissue. Those of skill in the peptide synthesis and related art will be familiar with such reagents, e.g. water-soluble carbodiimides and succinimides.

The coupling agent used in the preferred embodiments is 1-ethyl-3(3-dimethyl aminopropyl)carbodiimide hydrochloride (EDC), although other suitable coupling agents such as N-hydroxysuccinimide can also be used. The preferred coupling enhancer used in the embodiment where EDC is used as the coupling agent is N-hydroxysulfosuccinimide (sulfo-NHS), although other suitable coupling enhancers, such as HOBt and DMAP, can also be used. The concentration of the coupling agent and of the coupling enhancer can vary. However, appropriate concentrations are readily determinable by those of skill in the art. Preferably, the coupling agent is used in a concentration between about 10 mM and 500 mM, more preferably at about 100 mM or less, and most preferably at between about 20 mM and 50 mM. The coupling enhancer is preferably employed at between 0.5 mM and about 50 mM and more preferably at about 10 mM or less.

The cross-linking agents, the coupling agent and the coupling enhancer as well as their reaction products are preferably water-soluble. They should be selected such to maximize fixation and optimize cross-linking of the tissue, while minimizing the risks of damage to the prosthetic tissue during the fixation process, and of toxicity, inflammation, calcification, etc, after implantation. All solutions used for cross-linking are preferably filtered, before use, through 0.45 µm or less filters to minimize risks of contamination.

Reaction conditions for the cross-linking of the prosthesis may vary, depending on the cross-linking, coupling and enhancing agents employed. In general, the cross-linking process is carried out in an aqueous buffer selected from among those well known to those of ordinary skill in this art as to provide the most efficacious cross-linking reaction, while minimizing risks of calcification. Examples of suitable buffers include, but are not limited to, N-2-hydroxyethylpiperazine-N'-ethanesulfonic acid (HEPES) and 3-(N-morpholino)propanesulfonic acid (MOPS), and the like.

The pH and concentration of the buffered solution can vary, again depending upon the cross-linking, coupling and enhancing agents employed. Preferably, the buffer concentration and pH are chosen to provide the most effective cross-linking reaction while being the least harmful to the prosthesis. For example, with EDC as the coupling agent and sulfo-NHS as the coupling enhancer, the pH of the treatment solution is maintained at between about 6.0 to about 7.4. The reaction temperature may be between about 40° C. and 0° C.; preferably, the reaction is simply carried out at room temperature, e.g. between about 21 and 25° C.

Typically, the fresh prosthetic tissue to be fixed by the one-step cross-linking method of the present invention is kept on ice until it can be rinsed several times in ice-cold 0.85% saline or some other suitable solution. Such washing or rinsing is preferably carried out immediately after being excised from the donor animal, but in any event within 48 hours thereafter. If additional storage time is needed, the rinsed tissue is then stored, but preferably not longer than for 24 hours, in an appropriate buffer at a low temperature, such as about 4° C. No other pretreatment is required, nor is any desired that would alter the properties of such fresh tissue.

The surprising improvement in properties of the resultant fixed bioprosthetic device has been found to result from the use of a very large excess of the specified diamine cross-linking agent over and above the amount needed to effectively fix the bioprosthetic tissue. It has been surprisingly found that when about 4 to 5 times as much diamine cross-linking agent is used, compared to the highest amount mentioned in the '339 patent, to treat otherwise untreated (except for washing) fresh tissue, significant improvements result without any detrimental change in other advantageous properties of the resultant product. More specifically, the reduction in the surface area occurring during fixation, referred to hereinafter as Surface Reduction, is decreased by more than 50%, and the resistance of the product to calcification is dramatically increased. These advantages are obtained without any disadvantageous change in thermal denaturation, resistance to protease digestion or resistance to collagenase digestion.

The concentration of the diamine cross-linking agent is preferably between about 80 and about 135 millimolar, more preferably between about 90 and 130 millimolar, still more preferably between about 95 and 125 millimolar, and most preferably between about 100 and 125 millimolar. As previously indicated, the preferred diamine cross-linking agent has a carbon chain length not greater than 12 carbon atoms, e.g. between 4 and 8 carbon atoms, more preferably is a straight chain alkane having amine groups at its respective ends, and most preferably is 1,6-hexanediamine. Treatment of the animal tissue is preferably carried out by application of an aqueous solution containing the coupling agent, the coupling enhancer and the cross-linking diamine. The concentrations of the water-soluble coupling agent, preferably EDC, and the coupling enhancer, preferably sulfo-NHS, are as previously discussed, namely between about 10 mM and about 100 mM of EDC and between about 0.5 mM and about 10 mM of sulfo-NHS.

It is of course well known that before a bioprosthetic device can be implanted in a mammal, primarily a human, sterilization must be effected, and such is normally done as a final step prior to packaging. Accordingly, it is often important that tissue which advantageously suffered only minimal surface reduction during fixation does not thereafter shrink during sterilization. This is of course of particular importance for the treatment of replacement heart valves or the like where coaptation may be adversely affected (as opposed to raw materials that will be subsequently tailored into valves). Particularly effective sterilization processes for bioprosthetic material are described in Published International Applications WO 98/34650 (Aug. 13, 1998) and WO 01/10209 (Feb. 15, 2001). It has been shown that bioprosthetic materials, when subjected to fixation followed by sterilization for 48 hours at 40° C. in an aqueous solution of 25 mM EDC, still show only minimal surface reduction, and this remains true even if such sterilization is repeated 3 times. Such testing by employing repetition of the sterilization procedure is merely precautionary; on occasion, when bioprosthetic devices are being sterilized, if a target indicator that is included with the batch still shows positive, for whatever reason, at the end of the procedure, it may be necessary to repeat the sterilization procedure and, on rare occasions, even repeat it twice. Accordingly, it was felt prudent to measure surface reduction for tissue that had been subjected to such somewhat extreme conditions. It was also found that no significant shrinkage would occur when sterilization was carried out under treatment with a solution containing 20% isopropanol and 80% water that is 25 mM EDC and 100 mM of ethanolamine (a blocker) for 48 hours at 40° C.

The following examples describe experiments that were carried out to show the effectiveness of the invention and describe the best mode presently known to the inventors. However, it should be understood that these examples do not place limits upon the scope of the invention as the metes and bounds of the invention are set forth in the claims appended hereto.

EXAMPLE 1

This first experiment was carried out to show the effect of 1-6 hexane diamine concentration on surface reduction during cross-linking.

Eighty leaflets were excised from fresh porcine aortic roots. Each leaflet was blotted to remove excess buffer and placed flat, outflow side down, on a glass surface. Under a dissection microscope equipped with a reticule, the cusps were then marked in the radial and circumferential directions as shown in FIG. 1, with tissue marking dye following the manufacturer's recommendations. The distance between the center dot and each of the four exterior dots was 5 mm before cross-linking; therefore, the maximum distance between markers was 10 mm. The leaflets were then randomly distributed in 4 groups of 20 cusps each and cross-linked by incubation under the following conditions:

Group 1. Aqueous solution of 11.25 mM 1,6-hexanediamine (DIA) in 20 mM HEPES buffer, pH 6.5, containing 20 mM 1-Ethyl-3-(3-Dimethylaminopropyl)-Carbodiimide (EDC) and 1 mM N-hydroxysulfosuccinimide (Sulfo-NHS) for 96 hours at room temperature.

Group 2. Same as Group 1 but used 62 mM DIA.

Group 3. Same as Group 1 but used 112.5 mM DIA.

Group 4. The leaflets were incubated in a two step procedure according to the '339 patent. The first step was identical to Group 1 for 48 hours, and it was followed by a second step incubation with 7.5 mM suberic acid in the presence of 20 mM EDC/1 mM Sulfo-NHS.

After cross-linking was completed, the distances between the markers were again measured using a microscope equipped with a reticule for the radial and circumferential direction to calculate surface reduction. Calibration of the microscope was performed before each use. Size reduction was calculated, and the results are presented in Table 1.

TABLE 1

| Group number<br>Conditions | Surface Reduction<br>% of original (Mean +/− SEM) |
|---|---|
| 1. DIA = 11.25 mM | 8.00 +/− 0.9 |
| 2. DIA = 62 mM | 6.60 +/− 1.3 |
| 3. DIA = 112.5 mM | 2.73 +/− 0.81 |
| 4. DIA 11.25/SUA 7.5 mM | 12.2 +/− 0.9 |

In this experiment, the two-step fixation samples, i.e. Group 4, showed a 12% reduction in surface area as compared to only about 3% for Group 3. In an experiment using comparable conditions, the shrinkage of glutaraldehyde-fixed leaflets was found to be 5% and higher. The results demonstrate that a significant reduction in leaflet shrinkage is obtained with increased DIA concentration, a result which is superior to glutaraldehyde fixation that has been the industry standard for at least two decades.

EXAMPLE 2

The following experiment was carried out to determine the effect of DIA concentration greater than 112.5 mM in cross-linking.

Twenty-one leaflets for each condition were excised from fresh porcine aortic roots. For each condition, seven roots plus their 3 respective excised leaflets were incubated for 96 hours at room temperature in 250 ml of an aqueous solution of 20 mM HEPES and either 112.5 mM or 160 mM DIA, in the presence of 20 mM EDC and 1 mM Sulfo-NHS. After incubation, the samples were washed with sterile saline and then sterilized 3 times for 48 hours at 40° C. with 25 mM EDC in the absence (0%) of, or in the presence of either 5% or 20% isopropyl alcohol. For one condition, 100 mM ethanolamine was added as a blocker during sterilization with a solution containing 20% isopropanol.

The results are presented in Table 2 and demonstrate that 3 consecutive sterilization treatments of the leaflets fixed with 112.5 mM DIA, in the absence of isopropyl alcohol, do not induce significant shrinkage of the tissue, i.e. as compared to Table 1 for 112.5 mM DIA. Sterilization with the addition of either 5 or 20% alcohol does result in some shrinkage; however, addition of 100 mM ethanolamine when sterilization is being carried out in the presence of 20% isopropyl alcohol (when shrinkage would otherwise be the greatest) significantly inhibits such shrinkage from repeated sterilization. The data also indicate that increasing DIA concentration to 160 mM during the cross-linking step induced 14% tissue shrinkage that remained (which was unaffected during sterilization in the absence or presence of isopropyl alcohol); this is an amount of shrinkage far greater than that resulting from standard fixing treatments.

TABLE 2

| DIA mM | Isopropyl alcohol % | Surface Reduction % of original (Mean +/− SEM) |
|---|---|---|
| 112.5 mM | 0 | 3.3 +/− 1.3 |
| 112.5 mM | 5 | 6.7 +/− 1.2 |
| 112.5 mM | 20 | 8.3 +/− 1.4 |
| 112.5 mM | 20 + "blocker" | 4.3 +/− 1.3 |
| 160 mM | 0 | 14.6 +/− 1.3 |
| 160 mM | 5 | 14.0 +/− 1.4 |
| 160 mM | 20 | 14.2 +/− 1.3 |

EXAMPLE 3

The next experiment was carried out to determine the effect of the duration of incubation on cross-linking of porcine aortic valves from three different standpoints.

Five groups of 4 valves each were incubated in an aqueous solution containing 20 mM HEPES, 112.5 mM DIA, pH 6.5, 20 mM EDC and 1 mM Sulfo-NHS for 3, 6, 24, 48 and 96 hours. The valves were then washed with sterile saline to eliminate any reaction byproducts. They were stored in 10 mM HEPES, 0.85% sodium chloride, pH 7.4, and 20% isopropyl alcohol until use. Thermal denaturation tests and tests for resistance to proteolytic degradation by collagenase and by protease were performed for the determination of cross-linking efficacy. These test procedures are described in the *J. Heart Valve Dis.* 1996; 5(5):518-25. Fresh porcine aortic roots were used as a control.

a. Thermal Denaturation

Figure 2:
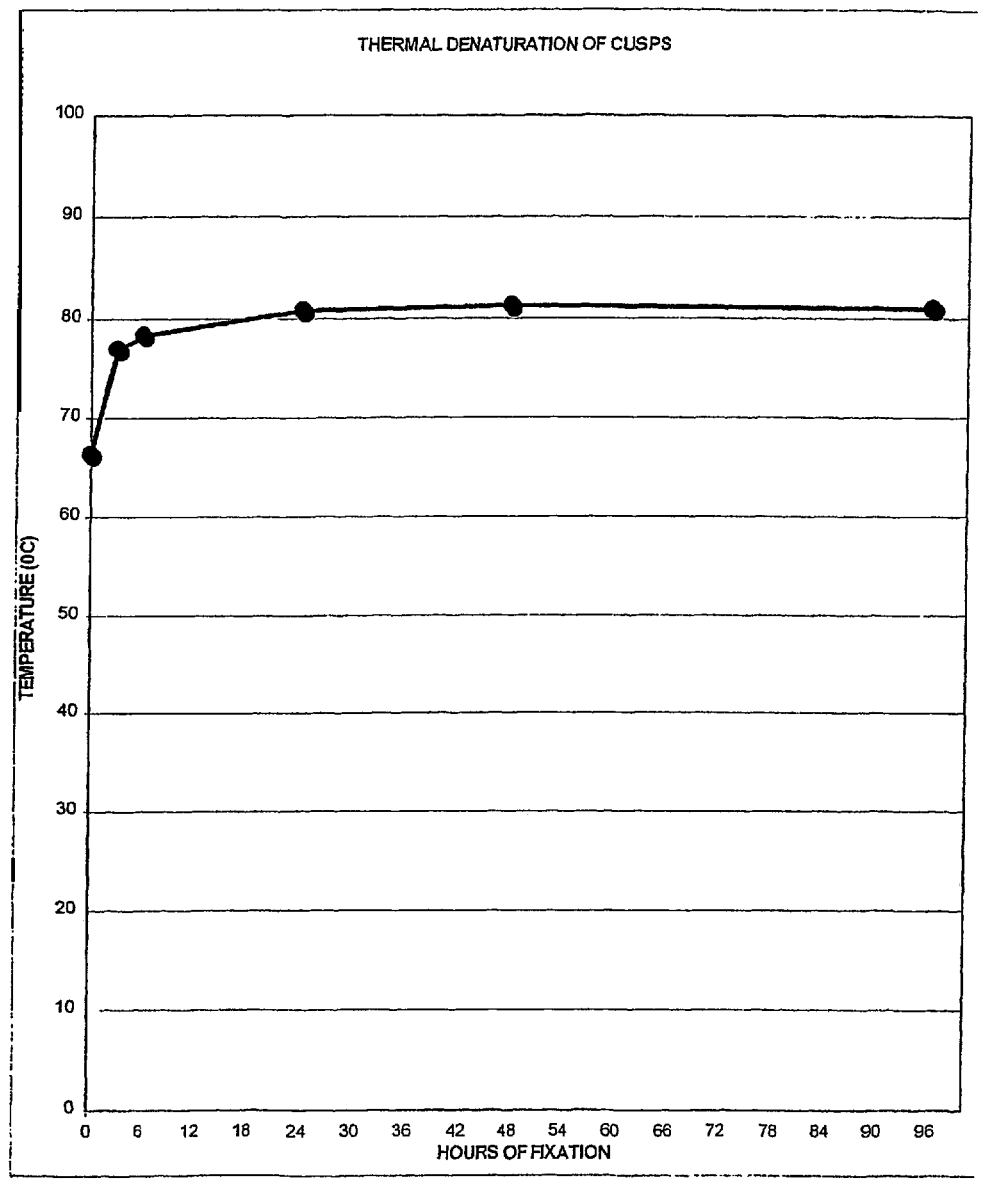
FIG. 2 is a graph which shows the effect of duration of fixation upon the thermal denaturation of porcine leaflets.

The leaflets were excised from the aortic roots and submitted (n=3 per condition) to thermal stability testing as described in the above reference. The results are shown in FIG. 2 and indicate that cross-linking of the cusp tissue occurs reasonably rapidly with that maximum stability to thermal denaturation being achieved at about 24 hours of incubation, with little change occurring thereafter.

b. Resistance to Digestion by Protease.

Figure 3:
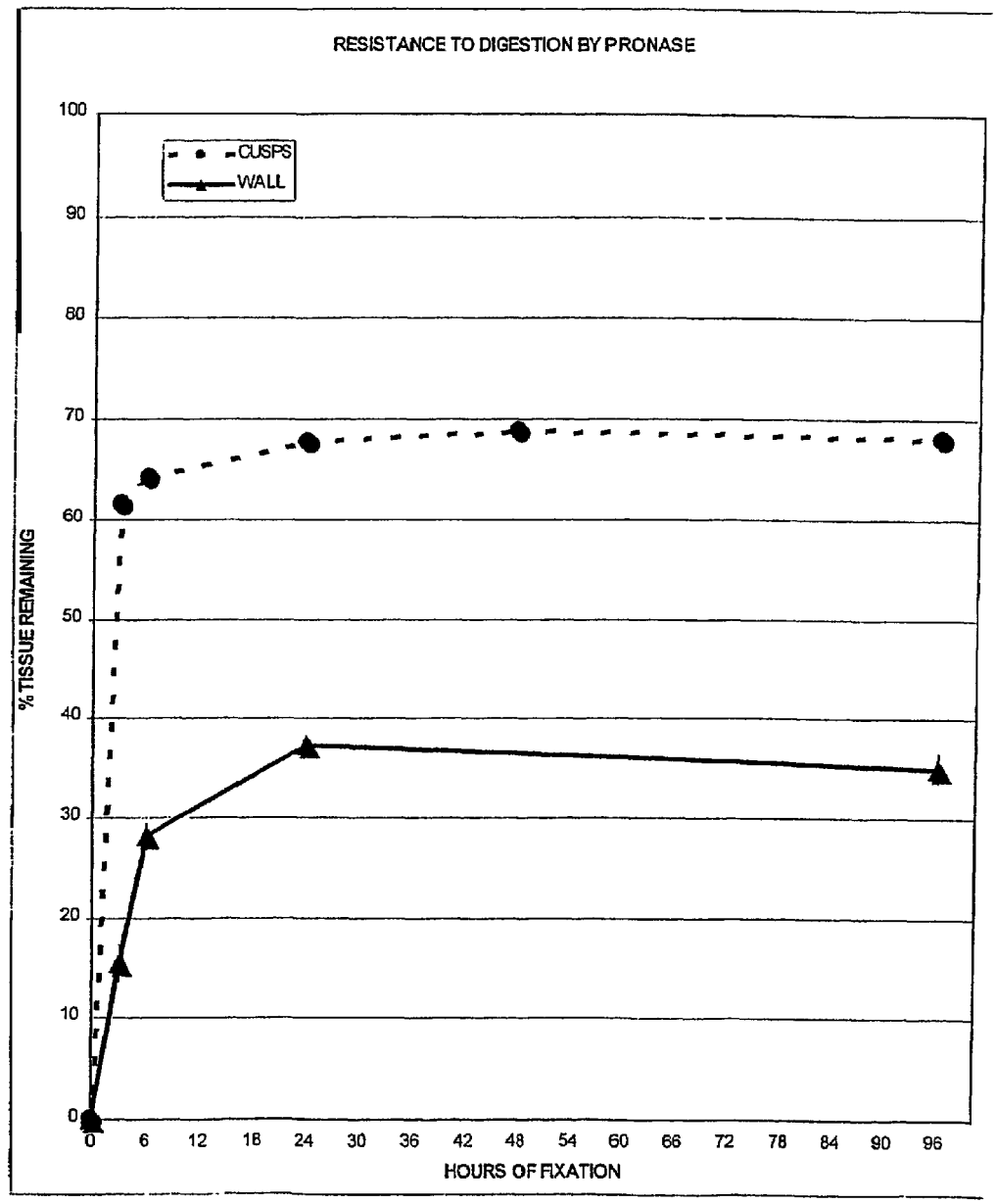
FIG. 3 is a graph which shows the resistance to digestion by proteolytic enzymes of wall tissue and of leaflets, relative to duration of fixation.

The leaflets (9 per condition) and coupons of aortic wall (12 per condition) were submitted to protease digestion at 50° C. for 24 hours according to the test described in the above reference. The results are presented in FIG. 3 and indicate that maximum resistance to digestion of both cusps and aortic wall occurs after about 24 hours of cross-linking.

c. Resistance to Digestion by Collagenase.

Figure 4:
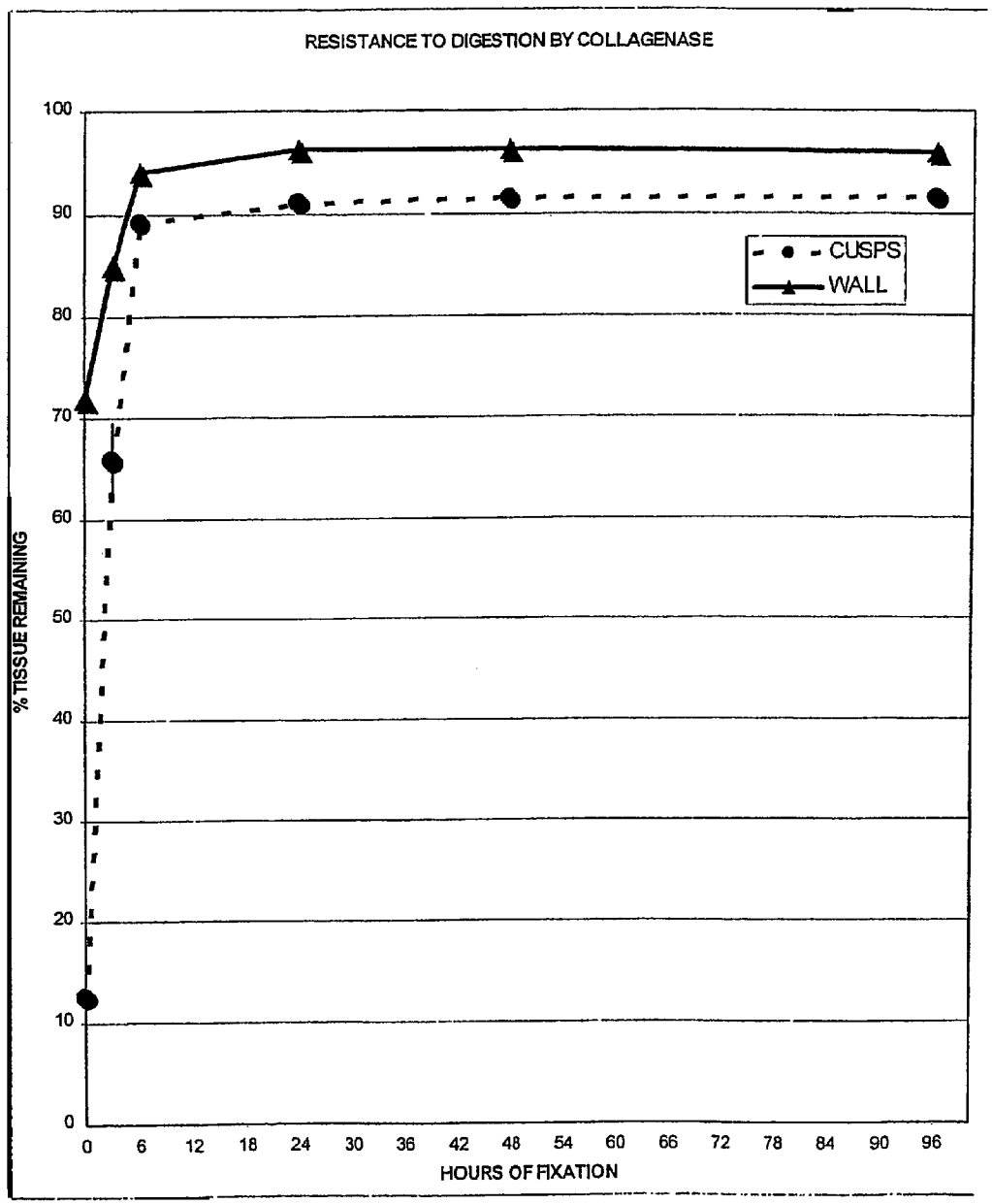
FIG. 4 is a graph which shows the resistance to digestion by collagenase of wall tissue and of leaflets, based upon duration of fixation.

The leaflets (9 per condition) and coupons of aortic wall (12 per condition) were submitted to collagenase digestion at 37° C. for 72 hours according to the test described in the above reference. The results shown in FIG. 4 demonstrate that maximum resistance is substantially obtained after approximately 24 hours of fixation and that resistance is only minimally improved as a result of treatment for another 24-hour period.

EXAMPLE 4

Following the good results obtained in Example 3, an experiment was carried out to compare tissue cross-linked using EDC and 112 mM DIA to standard glutaraldehyde-fixed tissue, generally using the same test regimens as in Example 3.

Porcine aortic roots were cross linked using an aqueous solution of 112 mM DIA, 20 mM HEPES buffer, pH 6.5, 20 mM EDC and 1 mM Sulfo-NHS. After 96 hours of incubation at room temperature, the valves were extensively washed with sterile saline to remove unreacted reagents and any reaction byproducts. The valves were sterilized 3 times according to the method of sterilization of Example 2, using 20% isopropanol. Standard glutaraldehyde-fixed and un-fixed porcine aortic roots were provided by Medtronic Heart Valves in Santa Ana, Calif. Leaflets and aortic wall coupons (5 mm×5 mm) were excised and submitted to the tests of cross-linking as generally described in Example 3. In addition, leaflets and aortic wall coupons were implanted subdermally in young rats for 8 weeks to evaluate resistance to calcification.

a. Thermal Denaturation

The results of thermal denaturation of leaflets are presented in Table 4 A. The thermal denaturation temperature for fresh leaflets, (i.e. non-fixed leaflets) and glutaraldehyde-fixed leaflets were found to be 65.5° C. and 84.9° C., respectively, which is consistent with previous test results. The thermal denaturation temperature determined for EDC cross-linked leaflets is 80.5° C. which represents a significant increase of 15° C. over fresh tissue. Although slightly lower than glutaraldehyde-fixed leaflets, such is felt to be fully acceptable. This lower denaturation temperature along with the kinetic differences mentioned earlier indicate that EDC cross-linking in the presence of 112 mM DIA induces different cross-links than those of glutaraldehyde-fixing.

TABLE 4 A

| Denaturation Temperature (° C., Mean +/− SEM) | | |
|---|---|---|
| EDC cross linking (n = 6) | Glutaraldehyde-fixed (n = 6) | Fresh (n = 4) |
| 80.5 +/− 0.3 | 84.9 +/− 0.4 | 65.5 +/− 0.1 | b. Resistance to Protease Digestion

A slightly stronger than usual test solution was used for this test; 242 mg of pronase was dissolved in 250 ml of solution rather than only 150 mg. The results of resistance to protease digestion are presented in Table 4 B. Fresh tissue is completely digested after 24 hours of incubation. There is no significant difference between carbodiimide fixation using this high diamine concentration and standard glutaraldehyde cross-linking for both cusps and aortic wall with respect to resistance to protease digestion. These results suggest that this cross-linking method is as effective as glutaraldehyde-fixing.

TABLE 4 B

| | Resistance to Protease digestion (% weight remaining, Mean +/− SEM) | | |
|---|---|---|---|
| | EDC cross linking | Glutaraldehyde-fixed | Fresh |
| Cusps (n = 12) | 72.0 +/− 2.4 | 75.3 +/− 4.2 | 0 |
| Aortic wall (n = 12) | 28.0 +/− 0.8 | 26.3 +/− 2.1 | 0 | c. Resistance to Collagenase Digestion

The results of resistance to collagenase digestion are shown in Table 4 C. Fresh leaflets, composed mainly of collagen, are fully digested; however, a significant portion of each aortic wall remains. With respect to the cusps, there is no significant difference between EDC-fixed and the glutaraldehyde-fixed tissue; however, it seems that the glutaraldehyde-fixed wall tissue is slightly less resistant to collagenase digestion than the EDC-fixed tissue. Overall, the results show that tissue cross-linked with EDC and 112 mM DIA is at least as resistant to collagenase as is tissue cross-linked with glutaraldehyde.

TABLE 4 C

Resistance to Collagenase Digestion
(% weight remaining, Mean +/− SEM)

|  | EDC cross linking | Glutaraldehyde-fixed | Fresh |
|---|---|---|---|
| Cusps (n = 12) | 94.6 +/− 5.6 | 97.6 +/− 5.7 | 0 |
| Aortic wall (n = 12) | 96.2 +/− 0.8 | 79.7 +/− 5.5 | 72.0 +/− 0.9 | d. Calcification After 8 Weeks Implantation in Young Rats.

Leaflets and wall coupons (1 cm×1 cm) were dissected from sterilized porcine aortic roots. The samples were washed 3 times for 2 minutes with sterile saline and then randomly implanted subdermally in young rats. After 8 weeks, the samples were retrieved, washed and submitted to quantitative calcium analysis as described in the above-mentioned reference.

TABLE 4 D

Calcification
($Ca^{++}$ mg/g of dry sample, Mean +/− SEM)

|  | EDC cross linking | Glutaraldehyde-fixed |
|---|---|---|
| Cusps (n = 9) | 11.2 +/− 6.8 | 216.5 +/− 5.8 |
| Aortic wall (n = 9) | 39.9 +/− 2.6 | 82.1 +/− 4.6 |

The results presented in Table 4 D indicate that tissue cross-linked with EDC in the presence of 112 mM DIA, whether cusps or aortic walls, is very significantly more resistant to calcification than glutaraldehyde-fixed tissue.

Furthermore, aortic wall calcification was not only significantly lower than it was for glutaraldehyde-fixed aortic wall tissue, but it was also lower than comparable aortic wall tissue fixed as described in the '339 patent. The above-reported calcium level in wall tissue after 8 weeks of implantation is slightly below the levels previously seen after implantation for just 4 weeks. Previously after 8 weeks implantation, the calcium level in such aortic walls was around 80 mg $Ca^{++}$ per g of sample, which is a level substantially twice that now found in the present sample, and one that is considered to be clinically significant.

The results obtained in the foregoing examples show the effectiveness of the invention in minimizing the reduction in surface area that occurs as a result of a one-step fixation that has been carried out to improve the characteristics of bioprosthetic material, e.g. its thermal denaturation, its resistance to protease digestion, and its resistance to collagenase digestion. In this respect, for the last few decades, glutaraldehyde-fixing has been the generally accepted standard, and therefore comparison may fairly be made with glutaraldehyde-fixation of the same tissue. It has thus been shown that the characteristics of tissue treated using the improved fixation process compare favorably with the characteristics of the same tissue when treated with glutaraldehyde for 7 days in these three aspects. Example 3 also shows that it appears that the effects of fixation using this process are essentially maximized after incubation for about 24-48 hours and that further treatment, although not detrimental, may not be necessary. This 24-hour term of achieving ultimate cross-linking can also be contrasted with other cross-linking procedures which are substantially complete after an hour or 2 duration, indicating that different cross-linking is very likely occurring, as the present process relies upon penetration deeply into fresh tissue over time. Therefore, although it can be seen that a very substantial improvement in properties is obtained after treatment for 8 hours, preferably the EDC-high amine concentration fixation is carried out at about room temperature for a period of at least 24 hours. Perhaps the most dramatic improvement occurs in the calcification resistance, which in many respects is one of the most important characteristics of a bioprosthetic device, inasmuch as calcification has been shown to be one of the primary causes of failure in prosthetic heart valves, resulting in stenosis and regurgitation in its operation. Although fixation by the process described in the '339 patent earlier resulted in some improvement in calcification resistance over comparable glutaraldehyde-fixed bioprosthetic tissue, Table 4 D shows that aortic wall tissue exhibits a resistance to calcification about twice that of glutaraldehyde-fixed tissue and that leaflets treated in this manner show a resistance nearly 20 times as great. This surprising calcification-resistance is expected to impart extremely valuable durability to bioprosthetic devices including tissue treated in accordance with this invention.

Although the invention has been set forth with respect to certain preferred embodiments which constitute the best mode presently known to the inventors for carrying out the invention, it should be understood that various changes and modifications that would be obvious to one having ordinary skill in this art may be made without departing from the scope of the invention which is defined in the claims appended hereto. For example, although treatment is preferably carried out using an aqueous solution, other biocompatible solvents, or combinations of solvents, might instead be used as generally known in this art.

Particular features of the invention are emphasized in the claims which follow.

The invention claimed is:

1. A process of fixing animal tissue to render it suitable for implantation in living mammals, which process comprises
treating said animal tissue with an effective amount of a coupling agent which promotes the formation of amide bonds between reactive carboxyl moieties and reactive amino moieties, in combination with a coupling enhancer, and with a cross-linking agent containing at least two reactive amine moieties,
said cross-linking agent containing at least two reactive amine moieties and being present in an amount of at least about 80 millimolar, and said treatment being carried out in a manner which results in the formation of amidated links between said cross-linking agent and reactive moieties carried by the molecules of said animal tissue,
whereby said tissue is rendered resistant to protease digestion while incurring only minimal surface reduction during fixation and whereby the fixed tissue is highly resistant to calcification.

2. The process of claim 1 wherein said cross-linking agent containing at least two reactive moieties has a carbon chain of at least 4 carbon atoms.

3. The process of claim 2 wherein said cross-linking agent is 1,6-hexanediamine.

4. The process of claim 3 wherein said hexanediamine is present at a concentration of between about 90 and about 130 millimolar.

5. The process of claim 3 wherein said hexanediamine is present at a concentration of between about 100 and about 125 millimolar.

6. The process of claim 1 wherein both said cross-linking agent and said coupling agent are water-soluble.

7. The process of claim 6 wherein said coupling agent is 1-ethyl-3(3-dimethyl aminopropyl)carbodiimide hydrochloride (EDC).

8. The process of claim 1 wherein said treatment is carried out for at least about 24 hours at about room temperature.

9. A process of fixing fresh animal tissue to render it suitable for implantation in living mammals, which process comprises
   washing but not otherwise altering fresh tissue excised from a donor animal,
   treating said washed animal tissue with an effective amount of a cross-linking agent containing at least two reactive amine moieties and with a coupling agent, in combination with a coupling enhancer, which promotes the formation of amide bonds between reactive carboxyl moieties and reactive amino moieties,
   said cross-linking agent containing at least two reactive amine moieties and being present in an amount of at least about 80 millimolar, and said treatment being carried out in a manner which results in the formation of amidated links between said cross-linking agent and reactive moieties carried by the molecules of said animal tissue,
   whereby said tissue is rendered resistant to protease digestion while incurring only minimal surface reduction during fixation and whereby the fixed tissue is highly resistant to calcification.

10. The process of claim 9 wherein said cross-linking agent is 1,6-hexanediamine.

11. The process of claim 10 wherein said hexanediamine is present at a concentration of between about 90 and about 130 millimolar.

12. The process of claim 10 wherein said hexanediamine is present at a concentration of between about 100 and about 125 millimolar.

13. The process of claim 9 wherein said cross-linking agent and said coupling agent are present in aqueous solution.

14. The process of claim 13 wherein said coupling agent is 1-ethyl-3(3-dimethyl aminopropyl)carbodiimide hydrochloride (EDC).

15. The process of claim 9 wherein said treatment is carried out for at least about 24 hours at about room temperature.

16. The process of claim 9 wherein said treatment is carried out within 48 hours of its being excised.

* * * * *